(12) United States Patent
Katzman

(10) Patent No.: US 8,376,931 B2
(45) Date of Patent: Feb. 19, 2013

(54) VISUALIZING ABLATION CANNULA

(75) Inventor: Scott S. Katzman, Port St. Lucie, FL (US)

(73) Assignee: Orthopaedic Development, LLC, Wellington, FL (US)

( * ) Notice: Subject to any disclaimer, the term of this patent is extended or adjusted under 35 U.S.C. 154(b) by 1089 days.

(21) Appl. No.: 11/101,221

(22) Filed: Apr. 7, 2005

(65) Prior Publication Data
US 2005/0182293 A1    Aug. 18, 2005

Related U.S. Application Data

(62) Division of application No. 10/278,405, filed on Oct. 23, 2002, now Pat. No. 6,902,526.

(51) Int. Cl.
*A61B 1/00* (2006.01)

(52) U.S. Cl. ........ 600/104; 600/101; 600/129; 600/130; 606/167; 606/170

(58) Field of Classification Search ............. 606/13–16, 606/108, 159, 167, 170; 600/101, 104, 108, 600/109, 112, 123, 128–130, 153, 160
See application file for complete search history.

(56) References Cited

U.S. PATENT DOCUMENTS

| | | | |
|---|---|---|---|
| 958,854 A | 5/1910 | Bunn | |
| 3,709,211 A | 1/1973 | Hawkins | |
| 4,543,966 A * | 10/1985 | Islam et al. | 600/567 |
| 5,284,474 A | 2/1994 | Adair | |
| 5,454,782 A * | 10/1995 | Perkins | 604/20 |
| 5,649,547 A * | 7/1997 | Ritchart et al. | 600/566 |
| 5,718,237 A * | 2/1998 | Haaga | 600/564 |
| 5,827,323 A * | 10/1998 | Klieman et al. | 606/205 |
| 5,989,196 A * | 11/1999 | Chu et al. | 600/567 |
| 6,156,029 A * | 12/2000 | Mueller | 606/7 |
| 6,224,566 B1 * | 5/2001 | Loeb | 604/22 |
| 6,258,083 B1 * | 7/2001 | Daniel et al. | 606/15 |
| 6,572,563 B2 * | 6/2003 | Ouchi | 600/564 |

* cited by examiner

*Primary Examiner* — Ahmed Farah
(74) *Attorney, Agent, or Firm* — Steven M. Greenberg, Esq.; Carey, Rodriguez, Greenberg & O'Keefe

(57) ABSTRACT

A medical needle set for visualized tissue ablation within a subject's body includes a cannula and components configured for inclusion in the cannula, including a trocar for occlusion of the cannula lumen during needle placement, and a visualizing ablation probe used for simultaneous endoscopic viewing and ablation of tissue sites with a laser beam. The cannula can include a tissue-gripping surface for stabilization of the needle set on the target tissue. A surgical system for tissue ablation includes a visualizing ablation needle set operably connected to an endoscope and a laser. A surgical procedure using this system permits simultaneous visualization and ablation of tissues, including those of the facet joints of the spine.

6 Claims, 3 Drawing Sheets

VISUALIZING ABLATION CANNULA

CROSS-REFERENCE TO RELATED APPLICATIONS

This patent application claims the benefit under 35 U.S.C. §121 as a divisional of U.S. patent application Ser. No. 10/278,405, filed Oct. 23, 2002 now U.S. Pat. No. 6,902,526, entitled VISUALIZING ABLATION DEVICE AND PROCEDURE, the entire teachings of which are incorporated herein by reference.

BACKGROUND OF THE INVENTION

1. Statement of the Technical Field

The disclosed invention is in the field of medical devices and procedures. In particular, the disclosed invention pertains to a novel surgical device and its use for ablation of tissues associated with solid anatomical surfaces such as joints.

2. Description of the Related Art

Lower back pain (LBP) is a common musculoskeletal complaint of industrialized society with a reported 60-90% of the population experiencing at least one episode of LPB per lifetime. As such, LBP is a very common cause of disability in persons younger than 45 years, the second leading reason for visits to primary care physicians, and the most frequent cause of visits to orthopedic surgeons and neurosurgeons. As the most frequently reported work-related injury, LBP is the most costly of all medical diagnoses when the costs of time lost at work, long-term disability and medical and legal expenses are factored in. Over the past century, various structures associated with the spine and back muscles, including the dorsal root ganglia, dura, muscles of the lumbar spine and the facet joints, have been implicated as the source of chronic LBP. Many recent clinical studies implicate facet joints of the spine as the source of pain in LBP. The spine is composed of a series of functional units, each consisting of an anterior segment made up of two adjacent vertebral bodies and the intervertebral disc between them, and the posterior segment consisting of the laminae and their processes. Bones of the spine articulate anteriorly by intervertebral discs and posteriorly by paired joints. The paired joints, known as the facet or zygapophyseal joints, are formed by the articulation of the processes on the laminae of adjacent vertebrae. Thus the superior articular process of one vertebra articulates with the inferior articular process of the vertebra below to form the facet joint.

Facet joints are true synovial joints with a joint space, hyaline cartilage surfaces, a synovial lining, and a fibrous capsule. Nociceptive (pain-sensing) nerve fibers and autonomic nerves have been identified in the lumbar facet joint capsule and synovial folds in recent studies. Inflammation, injury, nerve entrapment and degenerative osteoarthritic changes in the joint tissues all can lead to pain originating in the facet joints. Facet joint pain may also arise secondary to vertebral disc degeneration, owing to facet-joint osteoarthritis that develops in response to the primary disc degeneration.

Pain cannot be felt if the nerve pathways that relay pain impulses to the brain are interrupted. Painful stimuli from the facet joints are carried by the medial branches of the dorsal primary rami. On the theory that facet joint-mediated LBP should not be perceived in absence of intact medial nerve pathways, denervation (neurotomy) of the dorsal medial nerve branch has been advocated for treatment of lumbar facet joint pain. Early methods included destruction of the nerves by injection of neurolysing agents; however in recent years radiofrequency (RF) ablation of these nerves is the most widely used technique for denervation of the facet joints.

The target of a needle used for facet joint nerve ablation in the lumbar region (L1-L4 levels) is the portion of the nerve on the dorsal surface of the transverse process just caudal to the most medial end of the superior edge of the transverse process. The approximate vicinity of the target nerves can be determined using fluoroscopic techniques in subjects lying prone on a fluoroscopy table. Specifically, in the RF ablation procedure, under radiographic guidance, an introducer cannula is positioned in the vicinity of the dorsal medial nerve. Ideally the cannula is positioned alongside the nerve, rather than with its point facing the nerve. Once the position of the cannula appears to be correct, based on the radiographic image and the "feel" of the target tissue, the surgeon introduces an RF electrode via the cannula, with the aim of positioning the electrode alongside the nerve. Following positive stimulation at low voltage that reproduces the subject's pain, an RF lesion is created by passing current through the electrode that raises the tissue temperature to 60-80 degrees centrigrade for 60-90 seconds. This portion of the procedure is quite uncomfortable and calls for judicious use of sedation and analgesics.

Existing devices such as RF probes used for denervation of facet joints are placed by surgeons using radiographic techniques (C-arm fluoroscopy) without the benefit of endoscopic guidance to ensure accurate positioning of the electrodes. In fact, proper placement of the needle tip in the complicated structure of a subject's spine requires great skill by the treating clinician. The needles may need to be withdrawn and re-inserted multiple times. Errors in needle placement can result in accidental impalement of structures such as the nerve root in the lower spine, presenting a serious medical risk to the subject.

The success of RF denervation procedures varies widely, with a lower end of 9%. Despite improvements in technological approaches and controls incorporated into later clinical assessments of the efficacy of facet joint denervation as a therapy for LBP, there continues to be a wide range of reported success rates. This wide variability in the procedure in the hands of different practitioners suggests unpredictability inherent in the procedure itself. The unpredictability may be a reflection of failure of existing methods to enable sufficiently precise localization of the target nerve prior to lesioning, combined with incomplete destruction of the pain-causing nerve fibers by the RF electrode.

SUMMARY OF THE INVENTION

The present invention is a medical device and method for laser-assisted ablation of tissue during endoscopic visualization of the ablation procedure. The device includes a needle set connected to a laser and an endoscope. As used herein, the term "visualizing ablation needle set" refers to the various components of the needle set. The needle set can include an outer cannula, used for placement at a tissue site requiring treatment, a trocar that can be included within the cannula and can be used to occlude the cannula during placement, and a visualizing ablation probe that can be included within the cannula, and can be used to observe and ablate the target tissue during treatment with the laser. As used herein, the term "tissue," as in "tissue site," "target tissue," "tissue ablation," "tissue treatment," and "tissue-gripping," refers to any organic material, structure or organ forming part of a subject's anatomy and includes but is not limited to bone, cartilage, loose and dense connective tissue, adipose tissue, nervous tissue, muscle tissue and internal organs.

The cannula of the needle set can be used for placement on a tissue site in a subject's anatomy. The cannula can be hollow and can define a longitudinal channel or lumen. The distal tip of the cannula can include a tissue-gripping surface to prevent slippage of the cannula, once positioned at the target site. The needle set can also include a removable trocar for occluding the lumen of the cannula during placement of the cannula at a tissue site within the subject's anatomy. In one aspect of the present invention, the trocar can be a tubular shaft having a pointed distal tip.

The needle set yet further can include a removable obturator which can be inserted into the longitudinal channel of the cannula. The obturator can be a rod surrounding one or more longitudinal channels used for the passage of tools to the cannula tip. Tools that may be passed into the obturator include an endoscopic tool used for visualization of the treatment area, and a laser tool, connected to a source of laser energy. As used herein, the term "visualizing ablation probe" refers to an obturator and the aforementioned tools contained within it. During an ablation procedure, the tip of the visualizing ablation probe can be aligned close to the tip of the cannula. A beam from the laser tool can be used to ablate a target tissue, such as a facet joint capsule, while the progress of the ablation procedure can be monitored on a video screen by endoscopy.

The invention further encompasses a method of using the visualizing tissue ablation needle set in a surgical procedure for endoscopic laser ablation of tissues. In an exemplary use of this procedure, a surgeon may achieve denervation of the pain-causing nerve fibers of the facet joints, thereby reducing LBP originating from the facet joints. The method allows for visualization of the facet joint tissue prior to and during application of a laser beam used for ablation of the nerves innervating the joint.

The advantages of incorporating an endoscopic tool into a tissue ablation needle set are several. After initial placement of the cannula with radiographic guidance, and following insertion of the visualizing ablation probe into the cannula, anatomical structures at the tip of the probe can be visualized on the screen of the endoscope. Accordingly, the accuracy of the initial needle placement with respect to the target tissue can be assessed directly, allowing for corrections of the needle position. This advantage eliminates or minimizes the need for repeated insertions of the probe near the target site. Similarly, during the ablation procedure performed with the laser tool, the clinician is able to directly visualize the extent of the laser lesioning during the application of the laser treatment, allowing for precise tailoring of the laser treatment according to the response of the particular subject's tissues.

A further advantage of a needle set having a cannula with a tissue-gripping surface is that the position of the cannula can be anchored on solid anatomical structures such as bone and fibrous tissue forming joint capsules. By gripping onto the bone or fibrous tissue, the tissue-gripping surface can prevent slipping of the cannula tip away from the intended site of treatment. This feature, particularly in conjunction with the ability to view the site of the target tissue by endoscopy, enables the practitioner to stabilize the ablation probe in the precise location of the target, once the target is located.

BRIEF DESCRIPTION OF THE DRAWINGS

There are shown in the drawings embodiments which are presently preferred, it being understood, however, that the invention is not limited to the precise arrangements and instrumentalities shown, wherein.

DETAILED DESCRIPTION OF THE PREFERRED EMBODIMENTS

The present invention is a medical apparatus and surgical procedure for the visualization and ablation of tissue in a subject's body. The apparatus can include a needle set, the needles set including an outer cannula, a trocar and a visualizing ablation probe. Whereas the cannula can be placed at a tissue site requiring treatment, the trocar can be included within the cannula and can be used to occlude the cannula during placement. Once the cannula has been positioned within the subject's body proximate to the target tissue, the visualizing ablation probe can be inserted into the cannula and used to observe and ablate the target tissue during treatment with a medical laser.

Figure 1:
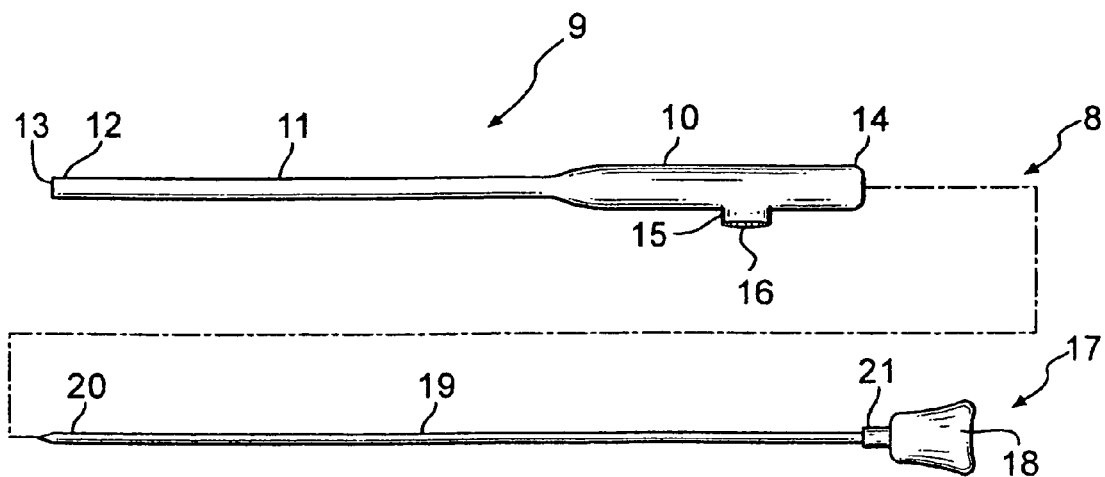
FIG. 1 is a schematic side elevation illustrating a visualizing ablation needle set including a cannula with a tissue-gripping distal tip and a trocar with a pointed tip.

Referring initially to FIG. 1, several features of the needle set of the invention are shown, including an embodiment of the cannula 8 with a distal tip 12 having a tissue-gripping surface 13. FIG. 1 also depicts an embodiment of the trocar 17 with a pointed tip 20. In the illustrated embodiment of the cannula 8, the shaft 9 can be a hollow tube having a proximal segment 10 wider than the distal segment 11. In other embodiments, the proximal segment 10 can be narrower than the distal segment 11, or of the same dimensions.

The lengths of the proximal and distal segments of the cannula shaft 9 can be varied according to the particular application. For example, in a specific embodiment of the invention useful for denervation of facet joints, the narrower distal segment of the cannula shaft 9 can be the only portion inserted into the subject's body. The "working distance" available for insertion of the cannula beneath the skin can be determined by the length of the distal segment 11.

Figure 2A:
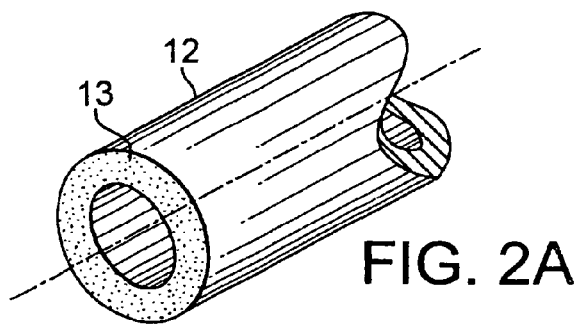
FIGS. 2A and 2B, taken together, are perspective views of a visualizing ablation needle set from the perspective of the distal tip.

A tissue-gripping surface 13 can be disposed at the distal tip of the cannula 12. This feature may be better appreciated in FIG. 2A, which shows a perspective view of the cannula distal tip 12, viewed from the distal end. The plane of the tissue-gripping surface can be perpendicularly positioned relative to the axis of the shaft, as in the particular embodiment shown in FIG. 2A, but other orientations of this surface are included within the invention. The tissue-gripping components can include teeth which protrude from the end of the shaft. In a specific embodiment shown in FIG. 3, eight teeth 44 are evenly spaced about the circumference of the wall of the cannula shaft in a crown arrangement; however many other numbers, shapes and arrangements of teeth, or other protrusions or surfaces capable of adhering to tissues, can be envisioned and are within the scope of the invention.

Referring again to FIG. 1, the proximal segment of the cannula shaft 10 can be open at its proximal end 14. The proximal end 14 can be suitably fitted for attachment of components of the needle set designed for insertion into the lumen of the cannula shaft, e.g. the trocar 17 and the visualizing ablation probe. For example, in some embodiments of the invention, the interior of the proximal end 14 includes threading complementary to that on the trocar, enabling the trocar to be secured to the cannula by screwing it into the proximal end 14. Other means of attaching needle components to one another are known and can be used in the invention.

Some embodiments of the cannula 8 further include a side port 15 suitable for attachment of a suction device. The side port can be a hollow tube, connected to the proximal shaft segment 10, having an interior channel 16 in continuity with the lumen of the cannula shaft 10. The side port 15 can be oriented perpendicular to the shaft segment 10 or it may attach to shaft segment 10 at an angle. The suction port facilitates the application of suction to the treatment site, if desired, during the ablation procedure.

The needle set further includes a trocar 17 configured for insertion into the cannula 8 through the opening in the proximal end 14. As seen in FIG. 1, the trocar includes a handle 18, a shaft 19 and a tip 20 which is closed. The function of the trocar is to occlude the lumen of the cannula, thereby preventing the lumen from clogging with tissue during advancement of the needle set through the subject's body. As indicated by the dotted line in FIG. 1, the trocar can be inserted into the cannula and secured to the cannula proximal end 14 by a connecting means 21 on the trocar handle. The trocar and cannula are designed to be used as a set, with the trocar shaft 19 configured for inclusion within the lumen of the corresponding cannula.

Figure 2B:
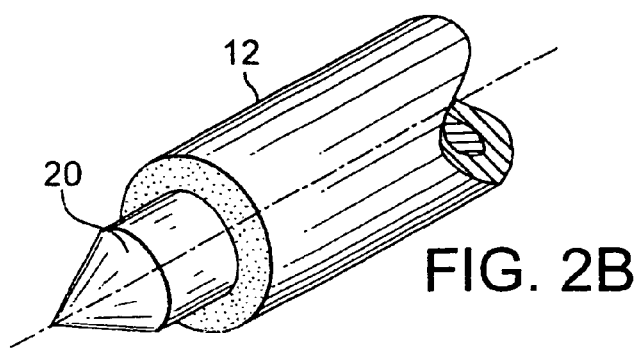

In some embodiments of the invention, it is desirable to have a trocar with a point at its tip 20, to facilitate penetration of the needle set through the subject's tissues. In such needle sets, the length of the trocar shaft 19 can be longer than that of the cannula shaft 9, such that the point on the trocar protrudes beyond the distal tip of the cannula when the trocar is secured in place within the cannula. FIG. 2B is a schematic diagram showing protrusion of a pointed trocar tip 20 from a cannula distal tip 12.

Figure 4:
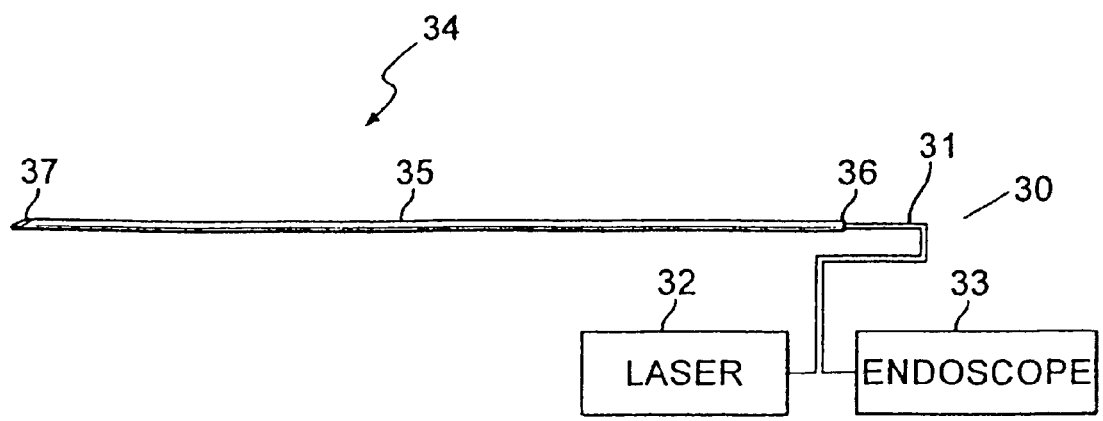
FIG. 4 is a schematic diagram of the visualizing ablation probe of the invention configured with an obturator and tools connected to an endoscope and a laser; and, FIG. 5 is a flowchart illustrating a procedure for facet joint tissue ablation according to the present invention.

FIG. 4 is a schematic diagram of the visualizing ablation probe 30 of the invention. As discussed previously, the probe can be coupled by connections 31 to a laser energy source 32 and to an endoscope 33. The visualizing ablation probe 30 includes an obturator 34 configured for inclusion in the cannula of the corresponding needle set. The obturator can be a supporting sleeve that includes a shaft 35 having one or more internal longitudinal channels open both at the proximal end of the shaft 36 and at its distal end 37.

The internal channels of the obturator enable the laser tool and the endoscope camera lens connections to be passed to the tip of the needle set, adjacent to the site of tissue treatment. As in the case of the trocar, the length of the obturator and its outside diameter can be configured to conform to the dimensions of the lumen of the corresponding cannula. In some embodiments of the obturator, the plane of the distal end 37 can be at right angles to the longitudinal axis of the shaft 35. In the specific embodiment shown in FIG. 4, the distal end can be cut at an angle. Endoscopic tools and laser tools, and combinations of the two, are known in the art. For example, in a particular embodiment of the invention suitable for facet joint ablation, a combination laser/endoscopic tool system can be suited for use with the visualizing ablation probe of the invention.

Figure 3:
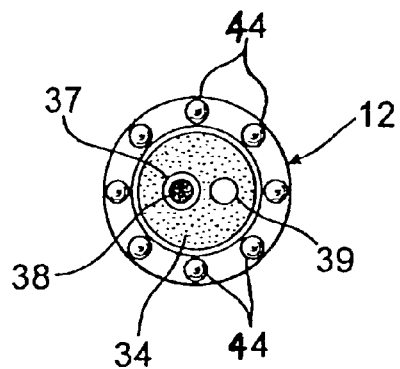
FIG. 3 is an end-on view of the distal tip of a visualizing ablation needle set having a visualizing ablation probe inserted therein.

Referring now to an end-on view of the distal tip of the invention shown in FIG. 3, the configuration of the needle set is seen when a visualizing ablation probe is inserted into the lumen of the cannula. In the specific illustrative embodiment shown, the obturator 34 contains two longitudinal channels. A laser endoscope channel 37 can be provided for passage of a bundled cable 38 containing both an endoscopic camera lens and a laser ablation tool. An injection channel 39 can be provided to enable delivery of a solution such as an anesthetic or an irrigation solution directly to the site of tissue ablation. The number, size and cross-sectional shape of the longitudinal channels in the obturator can be varied according to the particular application.

Figure 5:
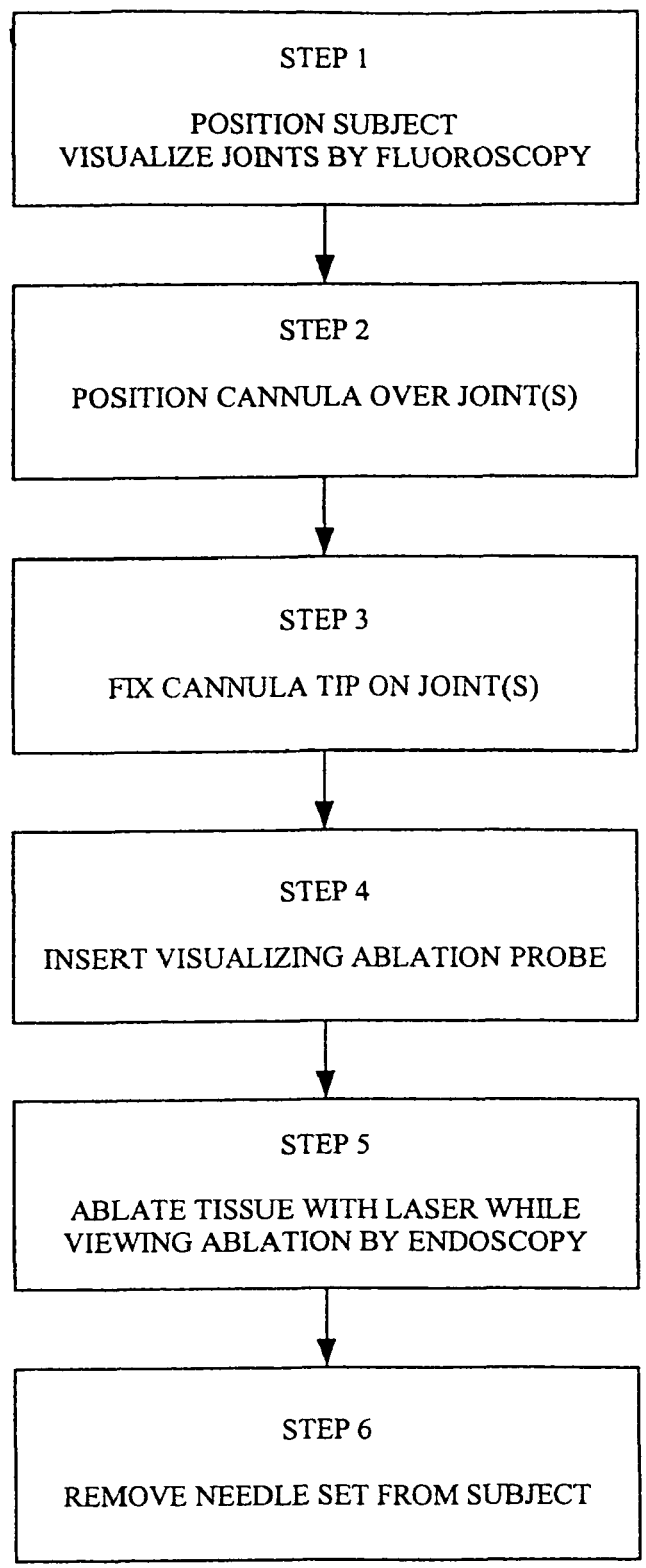

The invention also includes a method of using the visualizing ablation needle set in a surgical procedure for ablation of tissues in a subject's body. As an example of this procedure, a surgeon may achieve denervation of the pain-causing nerve fibers of the facet joints. The steps in a procedure for denervation of facet joints are shown diagrammatically in FIG. 5. Specifically, beginning in step 1, a subject in need of facet joint denervation can be brought to an operating room and placed in the prone position on a radiolucent table. A sterile preparation and drape is performed to the sites of the back to be treated.

A C-arm fluoroscope can be utilized to visualize the involved facet joints. Oblique projections can be used to visualize the ipsilateral side of the facet joints to be treated. Once a facet joint to be treated is identified in this manner, a local infiltrate of anesthetics (e.g. lidocaine with epinephrine) can be administered to the area. In step 2, a small scalpel can then be used to pierce the skin of the identified region. A cannula of a visualizing ablation needle set of the invention, with a trocar positioned within its lumen, can then be advanced through the skin and underlying muscle, and positioned on the facet joint. The position of the cannula can be photographed and viewed on the screen of the fluoroscope, and adjusted as necessary.

In step 3, once the position of the needle is satisfactory, pressure can be placed on the cannula. A tissue-gripping surface on the cannula tip can ensure that the cannula, once contacting the facet joint, is stabilized in the appropriate position over the target joint. The trocar can then be disengaged and removed with the right hand while the cannula is held with the left hand. In step 4, the visualizing ablation probe can then be passed into the cannula. Confirmation of proper placement of the needle set for facet denervation is now possible both by fluoroscopy and by direct visualization using the endoscopic camera. Visualization may be improved with an irrigation system which can be turned on at this point. Outflow can be accomplished by attaching a suction device to the side port of the cannula.

With the cannula thus stabilized on the facet, in step 5, the ablation procedure can be carried out while the area of treatment is directly visualized on the video monitor of the endoscope. Duration and energy levels of the laser treatment can be varied according to the particular application. As the facet joint capsule with its associated nerve tissue is ablated, the capsule tissue can be clearly visualized and seen to shrink and disappear. The ability to visualize the extent of tissue ablation while applying the laser beam enables the surgeon to tailor the ablation procedure to the characteristics of individual subjects' facet tissues, thereby ensuring that ablation is both accurate and complete. Finally, in step 6, when the ablation procedure is seen to be satisfactory, the cannula can be removed from the subject.

It should be noted that whereas certain exemplary embodiments of the visualizing ablation needle set and particular clinical applications have been discussed herein, the invention is not so limited, and its scope is to be determined according to the claims set forth below.

I claim:
1. A cannula comprising:
   a hollow shaft defining a longitudinal lumen, said shaft having a proximal segment and a distal segment, wherein said distal segment comprises a distal tip substantially aligned with the shaft to permit passage of a trocar within said hollow shaft, said distal tip being configured with a tissue-gripping surface wherein a plane of said tissue-gripping surface is substantially perpendicular to a longitudinal axis of said shaft.

2. The cannula of claim 1, wherein said proximal segment of said shaft is wider than said distal segment.

3. The cannula of claim 1, wherein said proximal segment of said shaft is narrower than said distal segment.

4. The cannula of claim 1, further comprising a side port disposed in said shaft, said side port having a configuration for attaching a suctioning device.

5. The cannula of claim 1, wherein said distal tip includes a plurality of tissue-adhering irregular surfaces protruding from said tissue-gripping surface.

6. The cannula of claim 5, wherein said tissue-adhering irregular surfaces are spaced apart on said tissue-gripping surface.

* * * * *